(12) United States Patent
Kirn

(10) Patent No.: US 8,979,771 B2
(45) Date of Patent: Mar. 17, 2015

(54) ACOUSTIC MYOGRAPHY SYSTEM AND METHODS

(75) Inventor: Larry J. Kirn, Austin, TX (US)

(73) Assignee: Articulate Labs, Inc., Austin, TX (US)

( * ) Notice: Subject to any disclaimer, the term of this patent is extended or adjusted under 35 U.S.C. 154(b) by 175 days.

(21) Appl. No.: 12/759,344

(22) Filed: Apr. 13, 2010

(65) Prior Publication Data

US 2010/0262042 A1 Oct. 14, 2010

Related U.S. Application Data

(60) Provisional application No. 61/168,669, filed on Apr. 13, 2009.

(51) Int. Cl.
*A61B 5/103* (2006.01)
*A61B 5/117* (2006.01)
*A61B 7/00* (2006.01)
*A61B 5/22* (2006.01)

(52) U.S. Cl.
CPC *A61B 7/006* (2013.01); *A61B 5/224* (2013.01)
USPC .......................... 600/587; 600/546; 600/586

(58) Field of Classification Search
USPC .......................................... 600/546, 586–595
See application file for complete search history.

(56) References Cited

U.S. PATENT DOCUMENTS

| | | | | |
|---|---|---|---|---|
| 3,157,781 A | * | 11/1964 | Gruen | 708/813 |
| 3,916,876 A | * | 11/1975 | Freeman | 600/546 |
| 4,748,987 A | * | 6/1988 | Barry | 600/586 |
| 5,143,069 A | * | 9/1992 | Kwon et al. | 600/437 |
| 5,755,675 A | * | 5/1998 | Sihvonen | 600/594 |
| 6,709,432 B2 | * | 3/2004 | Ferek-Patric | 606/41 |
| 2004/0082877 A1 | * | 4/2004 | Kouou et al. | 600/546 |
| 2004/0225211 A1 | * | 11/2004 | Gozani et al. | 600/382 |
| 2008/0159559 A1 | * | 7/2008 | Akagi et al. | 381/92 |

OTHER PUBLICATIONS

Article entitled "Acoustic Myography: A Non-invasive Monitor of Motor Unit Fatigue," to Barry et al., Muscle & Nerve, vol. 8, pp. 189-194, Mar./Apr. 1985.*

* cited by examiner

*Primary Examiner* — Rene Towa
(74) *Attorney, Agent, or Firm* — Trop, Pruner & Hu, P.C.

(57) ABSTRACT

Acoustic impulses from a muscle are converted into an electrical signal with a transducer such as a piezo film microphone, and analog or digital signal processing circuitry determines the density of self-similar spectral components of the signal and generating an output signal representative of the contractile force of the muscle based upon the density of the self-similar spectral components. The circuitry is used to determine self-similar spectral components of the signal and the density of those components, and the density is used to provide an output signal filtering. Different embodiments use combinations of filtering, Fourier analysis and correlation or auto-correlation. The self-similar spectral components may be pre-determined or determined through signal processing. The output signal may be used to calculate muscle contractile force, fatigue or other muscle conditions.

7 Claims, 5 Drawing Sheets

ACOUSTIC MYOGRAPHY SYSTEM AND METHODS

REFERENCE TO RELATED APPLICATION

This application claims priority from U.S. Provisional Patent Application Ser. No. 61/168,669, filed Apr. 13, 2009, the entire content of which is incorporated herein by reference.

FIELD OF THE INVENTION

This invention relates generally to electronic signal processing and, in particular, to methods and apparatus for qualification and quantification of acoustic emissions from muscle tissue.

BACKGROUND OF THE INVENTION

It has been known for quite some time that electrical motor nerve impulses directly result in muscle contraction. Resultantly, considerable research effort has been extended toward measurement of these electrical impulses for their direct use in situations wherein physical challenges thwart normal human skeletomuscular control. Although this research has become extremely fruitful in the diagnostic area of electromyography, use of these electrical nerve impulses for control of electrical or mechanical devices has met overwhelming obstacles. The electrical impulses are extremely low potentials, and are insulated in the body by myelin sheath. Resultantly, the reliability and useful dynamic range of these signals are poor. Being largely intermuscular, high-quality electrical motor nerve impulses (electromyography, or EMG pulses) have remained primarily accessible through use of needles, a practice made unpopular by pain.

In response to these nerve impulses, muscles emit mechanical noise, at an amplitude roughly equivalent to the force exerted. This correlation has resulted in limited use of acoustic information for diagnostic or replicative purposes, such as that shown by U.S. Pat. No. 4,748,987 "Acoustic Myography". Due to the extreme relative weakness of these resultant acoustic pulses against the environment, however, little use has been found for electrical/acoustic correlation.

High-quality motor nerve impulses, however, are in high demand for many applications, especially diagnostic and control. A need exists for a technique whereby high-quality motor nerve impulses may be externally quantified and qualified.

SUMMARY OF THE INVENTION

Exploiting the observation that muscle acoustic output is a direct, relatively instantaneous product of individual neuron impulses, this invention resides in a technique whereby measured muscle acoustic output is qualified and/or quantified by one or a combination of characteristics of motor nerve electrical impulses. Acoustic output so characterized can therefore be seen to accurately replicate the parent motor nerve electrical impulses, and therefore be quantitatively and qualitatively useful for diagnostic or control purposes. Advantageously, the functional dynamic range of a signal processed by the invention far exceeds that of the raw acoustic signal.

A system according to the invention for generating an electrical signal indicative of muscle activity comprises a transducer for converting acoustic impulses from a muscle into a corresponding electrical signal, and signal processing circuitry operative to determine the density of self-similar spectral components of the signal and generating an output signal representative of the contractile force of the muscle based upon the density of the self-similar spectral components. The transducer may be a microphone such as a piezo film microphone. The signal processing may be performed at least partially in the analog or digital domains, and the output signal may be analog or digital.

A method of generating an electrical signal indicative of muscle activity comprises the steps of: converting acoustic impulses from a muscle into a corresponding electrical signal; determining self-similar spectral components of the signal and the density of the self-similar spectral components; and using the density of the self-similar spectral components to provide an output signal representative of the muscle activity.

The ratio of signal-to-noise may be enhanced using various techniques, including filtering, Fourier analysis, and correlation or auto-correlation. Specific frequencies of the self-similar spectral components may be pre-determined or determined through signal processing. The output signal may be used to calculate muscle contractile force or other muscle conditions such as fatigue.

Although the amplitude of nerve impulses, and their resultant acoustic impulses, exhibit a very limited amplitude dynamic range, the pulse density (impulses per unit time) correlates well with exertion. The underlying principle effectively resides in the use of appropriate techniques to determine this density of qualified pulses, rather than to quantify their composite effect.

DETAILED DESCRIPTION OF THE INVENTION

Figure 1:
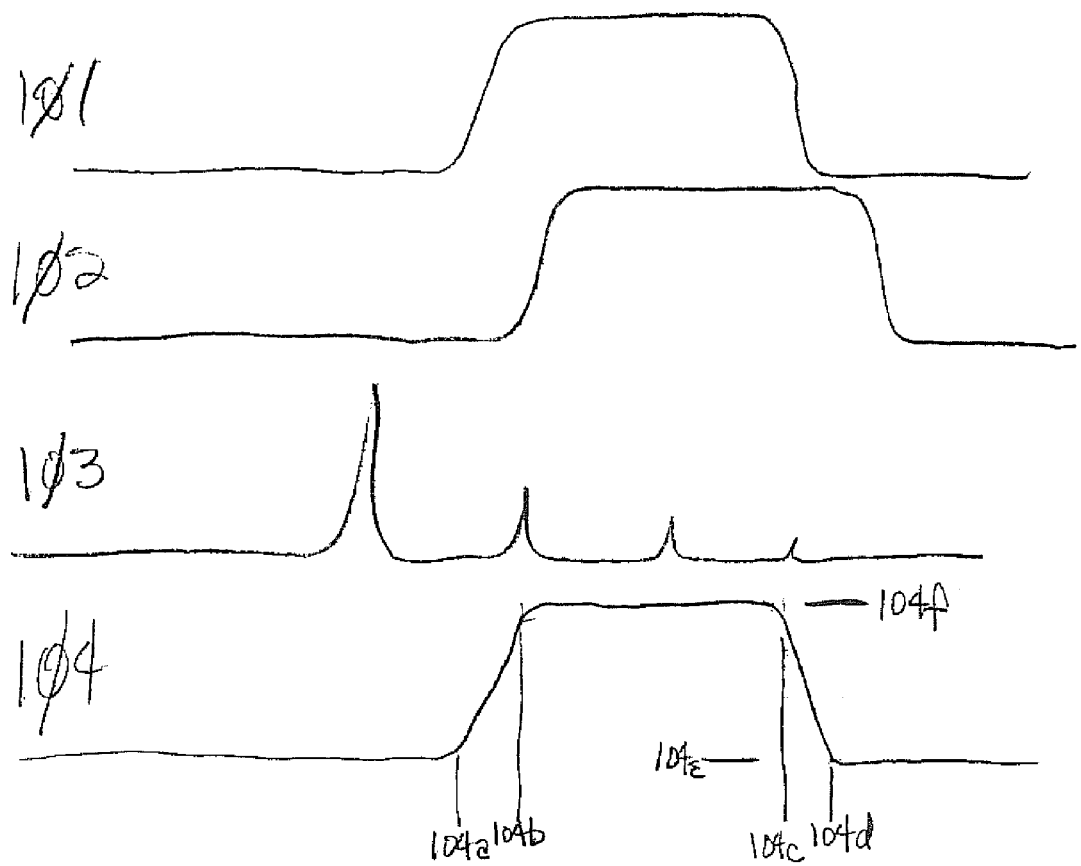
FIG. 1 shows a single electrical motor nerve pulse, the resultant acoustic pulse, and the spectrum, pulsewidth, and amplitude of the pulses.
Figure 2:
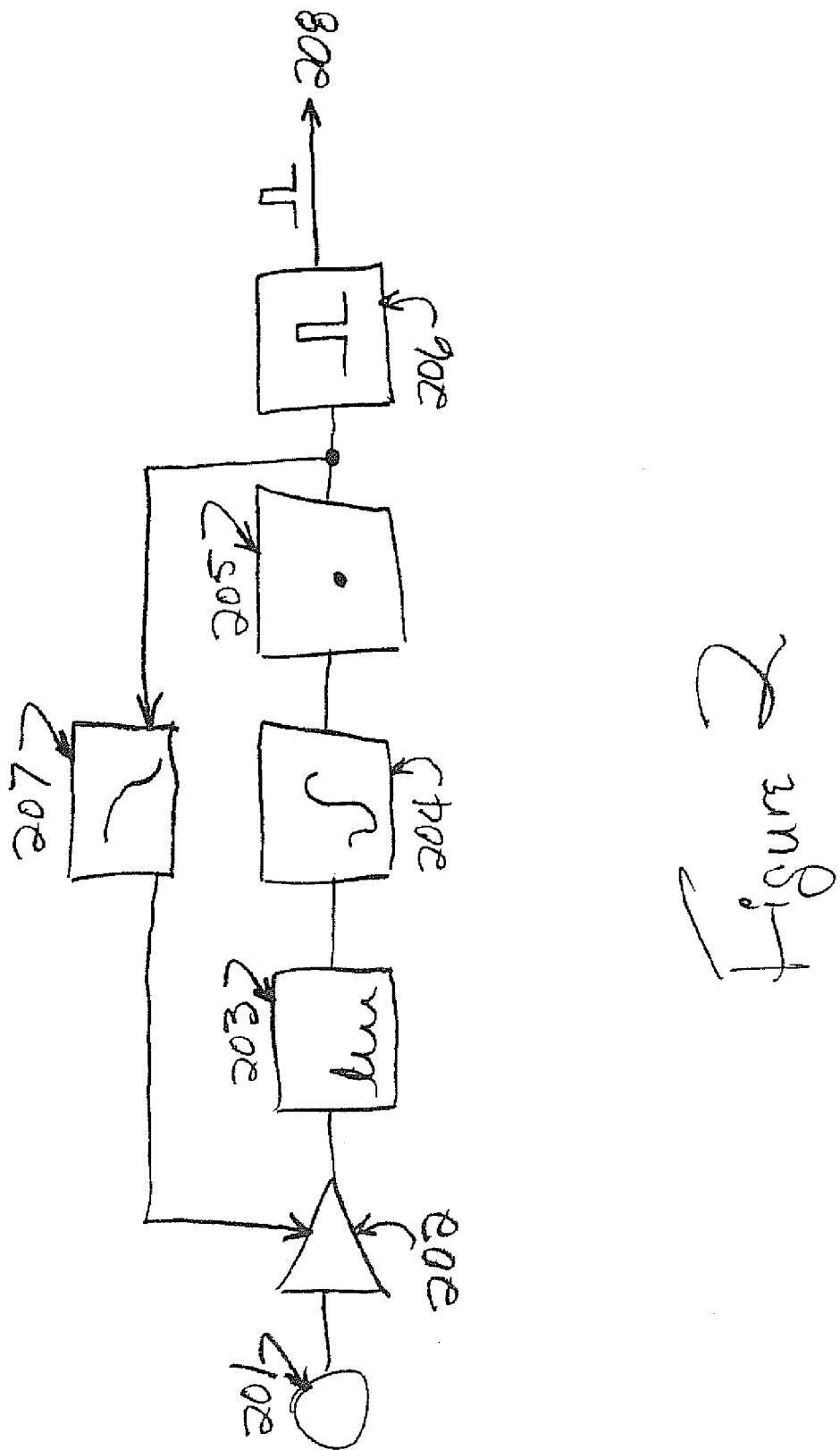
FIG. 2 shows a preferred embodiment of the present invention whereby an external acoustic measurement provides an accurate representation of the original internal electrical source through filtering techniques.
Figure 3:
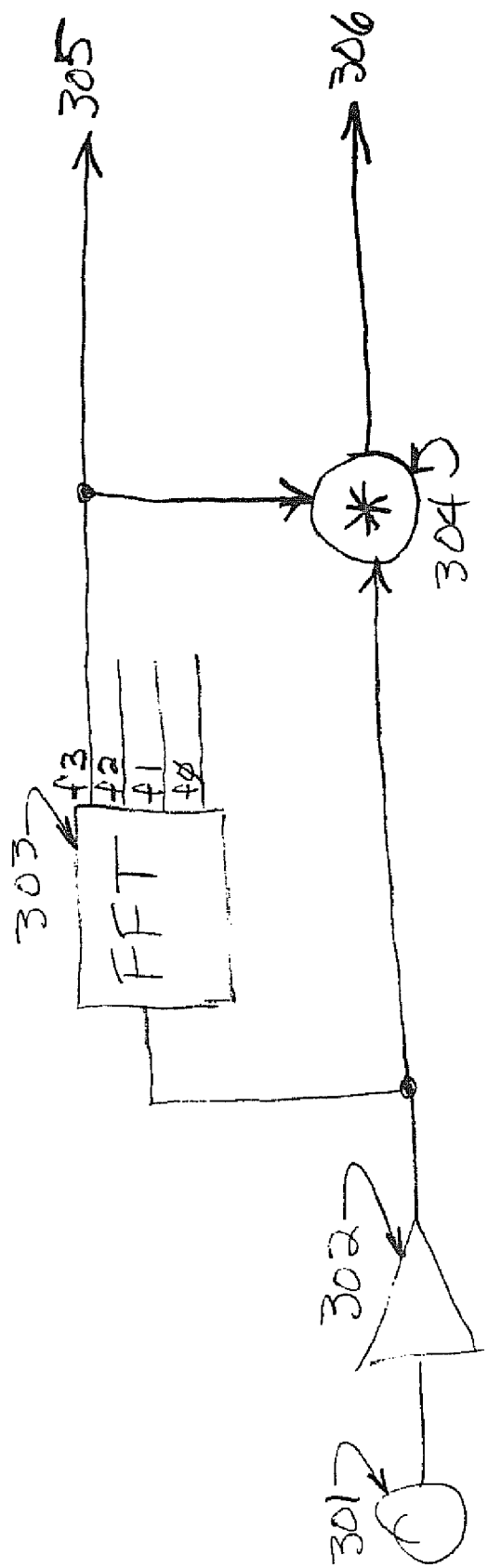
FIG. 3 shows a preferred embodiment of the invention employing a Fourier transform to surmise pulse density through average frequency.
Figure 4:
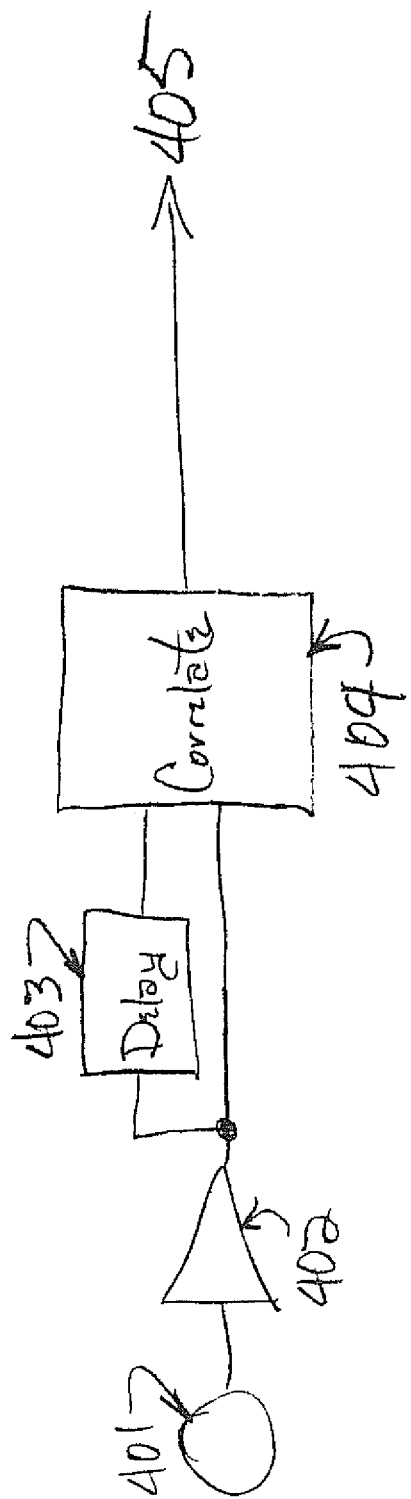
FIG. 4 shows a preferred embodiment of the present invention using autocorrelation to extract pulse density information.
Figure 5:
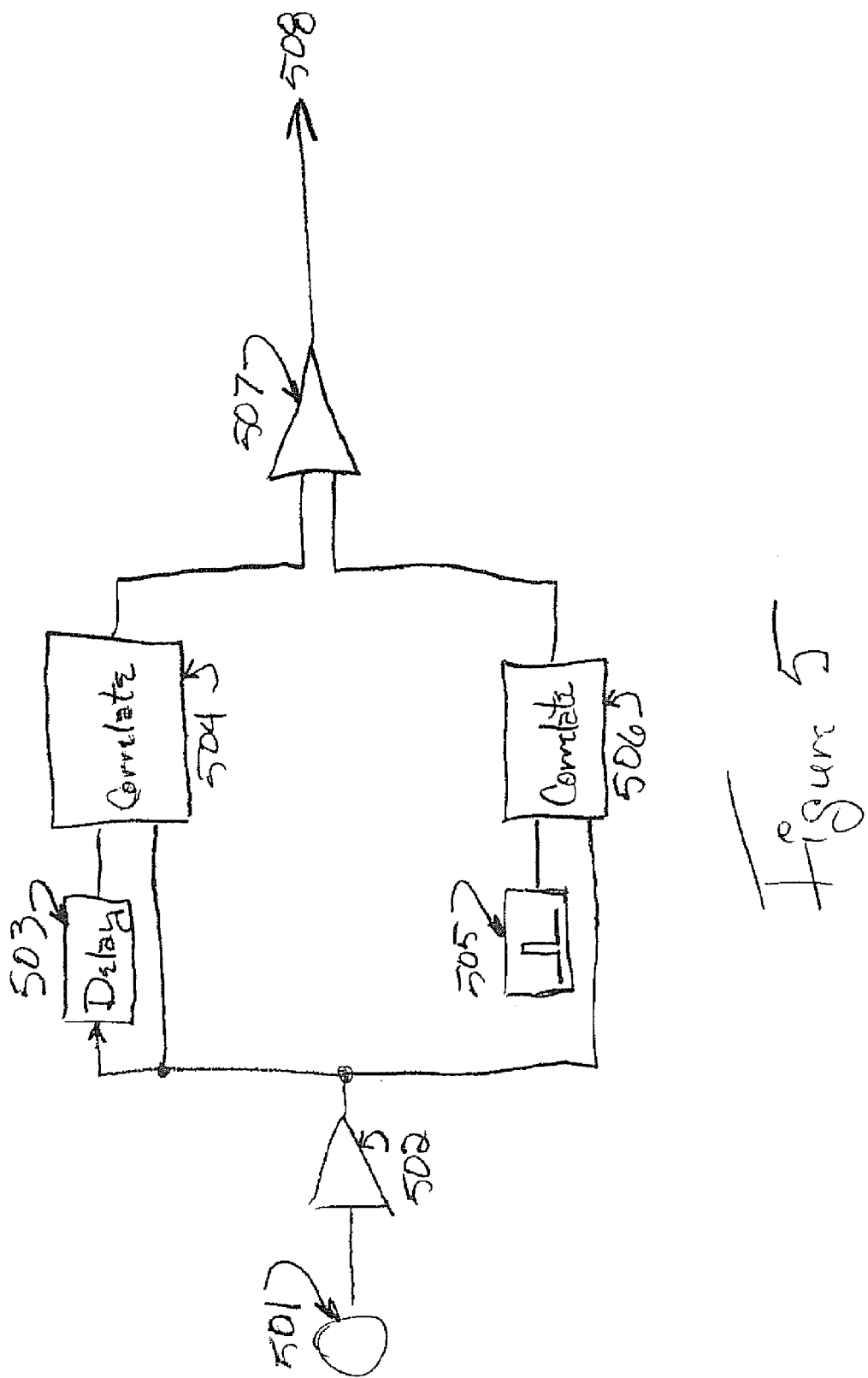
FIG. 5 shows an alternative embodiment of the embodiment of FIG. 4.

FIG. 1 is a diagram showing a single electrical motor nerve pulse, the resultant acoustic pulse, and the spectrum, pulsewidth, and amplitude of the pulses. FIG. 2 is s block diagram of an embodiment of the present invention whereby an external acoustic measurement provides an accurate representation of the original internal electrical source through filtering techniques. FIG. 3 depicts an embodiment of the invention employing a Fourier transform to surmise pulse density through average frequency. FIG. 4 shows the use of autocorrelation to extract pulse density information. FIG. 5 illustrates an alternative configuration of the embodiment of FIG. 4, showing impulse feature extraction through correlation and noise rejection through autocorrelation.

Referring now to FIG. 1, plot 101 shows the current (or voltage) waveform of a single pulse from an intermuscular motor nerve as a function of time. Note that a common characteristic of the nerve pulses is a relatively constant amplitude. Plot 102 shows a resultant muscle acoustic waveform. Plot 103 shows the spectral components of plot 101, expressed in relative amplitude versus frequency. Plot 104 shows detailed rise time from marker 104a to marker 104b, pulsewidth from marker 104b to marker 104c, fall time from marker 104c to marker 104d, and relative amplitude from level 104e to level 104f. Although by no means complete, this list will be seen to those skilled in the art as a basic characterization set for electrical phenomena.

Referring now to FIG. 2, the signal from microphone 201 is amplified by variable amplifier 202, the output of which is filtered by bandpass filter 203. Note that the passband definition of the filter 203 is configured to approximate the spectral components of plot 103 of FIG. 1. The output of bandpass filter 203 drives integrator 204, the integrated output of which in turn drives differentiator 205, the derived output of which drives both pulsewidth discriminator 206 and lowpass filter 207. The output of lowpass filter 207 provides gain control of variable amplifier 202, forming an automatic gain control (AGC) loop. The output of pulsewidth discriminator 206 yields final pulse approximation 208.

It can be seen that signal qualification attendant to each electrical characteristic of plot 101, shown in plots 103 and 104, of FIG. 1, are included in the processing path of FIG. 2. Furthermore, it should be apparent to one skilled in the art that, through the present technique, increasing the specificity of signal qualifications to match characteristics of nerve impulse 101 of FIG. 1 will preserve impulse replication despite increasing environmental adversaries such as noise.

Referring now to FIG. 3, microphone 301 converts acoustic muscle impulses to electrical impulses which are amplified by amplifier 302. Amplifier 302 provides the sum of impulses to Fourier transform 303 and as first input of multiplier 304. The highest frequency output f3 is supplied both as second input of multiplier 304 and as first output 305. The output of multiplier 304 is supplied as second output 306.

In that the input to microphone 301 consists of a sum of individual impulses at relatively constant amplitude, the average frequency of the composite spectrum resultantly increases proportional to the density. The highest frequency spectral output f3 of Fourier transform block 303 resultantly provides an output of pulse density at first output 305. In order to accommodate amplitude variations which are sometimes proportional to muscle intensity, multiplier 304 provides at second output 306 the product of their amplitude from amplifier 302, multiplied by the spectral density provided from highest frequency spectral output f3 of Fourier transform 303.

The embodiment of FIG. 3 features another attribute which proves important when the invention is used with multiple muscles. Sound waves travel faster through taut muscle than through flaccid tissue. Resultantly, instantaneous spectral components transmitted through taut muscle are higher than those through flaccid tissue. In that this phenomenon is independent of the innate impulse signature of the signals used by the invention, spectral content provides proximity information which is very useful in triangulation.

Referring now to FIG. 4, microphone 401 converts acoustic muscle impulses to electrical impulses which are amplified by amplifier 402. These amplified impulses are provided directly and in delayed form, through delay 403, to correlator 404, which provides output 405. The embodiment of FIG. 4 essentially performs finite-time autocorrelation of acoustic impulses from microphone 401 to extract the impulse nature of the desired signals, while rejecting noise which contains much less self-correlated information.

Referring now to FIG. 5, microphone 501 converts acoustic impulses to electrical impulses which are amplified by amplifier 502 and supplied as input to delay 503 and second inputs of correlators 504 and 506. The output of delay 503 is supplied as first input of correlator 504. Impulse feature 505 is supplied as first input of correlator 506, which outputs the correlation of these muscle impulses from microphone 501 with the characteristic defined by impulse feature 505 to the second input of differential amplifier 507. Simultaneous to operation of correlator 506, correlator 504 provides the correlation of these muscle impulses from microphone 501 with the delayed version of this same signal from delay 503, presumably at a much lower frequency than that provided by impulse feature 505. In that the output of correlator 504 is provided as first input to differential amplifier 507, self-correlated low frequency noise is subtracted by differential amplifier 507 from the higher-frequency impulse correlation provided by correlator 506. This subtraction then serves to further attenuate low-frequency noise, thereby improving selectivity of the desired impulse density itself.

With impulse replication so preserved by the present invention, secondary diagnostic characteristics of motor nerve impulses can more easily be observed externally. Additionally, it can be seen from this disclosure that qualification of the impulse nature of the muscle acoustic output greatly simplifies density determination, hence facilitating simple proportional muscle control signals of very broad dynamic range required of neuropathic diagnostic procedures or bionic/prosthetic device control. This dynamic range allows application in previously untenable areas, such as eye position sensors.

Although the embodiments shown measure and/or output signals representative of contractile force, body part positional information is readily obtained through differential use of the invention on the essentially differential muscle structure of the body. By use of the current technique, it can be seen that the acoustic analog of electrical motor nerve impulses may be used to provide accurate muscle contractile force and/or position, in a totally non-invasive fashion.

The invention claimed is:

1. A system to generate an electrical signal indicative of muscle activity, comprising:
 a transducer operative to convert acoustic impulses emitted from a muscle into a corresponding electrical signal; and
 signal processing circuitry operative to (a) delay a first portion of the signal in time domain, which is present at a first moment in time, by a known delay amount to produce a time-shifted instance of the signal in the time domain; (b) correlate a second portion of the signal in the time domain, which is present at a second moment in time that follows the first moment in time, with the time-shifted instance of the signal in the time domain to produce a correlation and (c) generate an output signal in the time domain, which is representative of a contractile force of the muscle based upon density of impulses extracted by the correlation;
 wherein the signal processing circuitry includes a first correlator to produce the correlation; a second correlator in parallel with the first correlator to correlate the second portion of the signal with an impulse feature in the time domain; and a differential amplifier, having inputs driven by the first and second correlators, to remove low frequency noise.

2. The system of claim 1, wherein the signal processing circuitry is operative to perform at least partially in the analog domain.

3. The system of claim 1, wherein the signal processing circuitry is operative to perform at least partially in the digital domain.

4. The system of claim 1, wherein the output signal is in digital form.

5. The system of claim 1 wherein the signal processing circuitry includes an autocorrelator to qualify acoustic impulses within the signal.

6. The system of claim 1 wherein the acoustic impulses result from generally non-periodic nerve impulses.

7. The system of claim 1 wherein the acoustic impulses result from generally non-periodic nerve impulses with previously unknown frequencies.

* * * * *